United States Patent [19]

Vofsi et al.

[11] 4,207,417
[45] Jun. 10, 1980

[54] PHOSPHORUS CONTAINING POLYOLS

[75] Inventors: David Vofsi; Martin M. Halmann; Saul Yanai, all of Rehovot, Israel

[73] Assignee: Yeda Research & Development Co. Ltd., Rehovot, Israel

[21] Appl. No.: 858,901

[22] Filed: Dec. 8, 1977

[30] Foreign Application Priority Data

Dec. 28, 1976 [IL] Israel .................................. 51178

[51] Int. Cl.² ............................................ C07H 13/00
[52] U.S. Cl. .................................. 536/117; 260/338; 260/340.7; 260/953; 260/969; 536/1; 521/108; 521/109
[58] Field of Search ............... 536/117; 260/338, 953, 260/969, 340.7

[56] References Cited

U.S. PATENT DOCUMENTS

| | | | |
|---|---|---|---|
| 3,153,036 | 10/1964 | Merten et al. .................. | 536/117 |
| 3,184,495 | 5/1965 | Baranauckas et al. ............ | 260/969 |
| 3,333,026 | 7/1967 | Larrison ........................ | 260/969 |
| 3,382,236 | 5/1968 | Guttag .......................... | 536/117 |
| 3,382,301 | 5/1968 | Hechenbleikner et al. ......... | 260/953 |
| 3,524,846 | 8/1970 | Moffatt et al. .................. | 536/117 |
| 3,760,038 | 9/1973 | Lewis ........................... | 260/969 |
| 3,803,270 | 4/1974 | Iliopulos ....................... | 260/953 |

Primary Examiner—Johnnie R. Brown
Attorney, Agent, or Firm—Browdy and Neimark

[57] ABSTRACT

Polyhydroxylated O,O-dialkyl phosphonoacetals having the formula

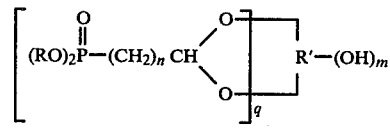

wherein
R is an alkyl group having from 1-3 carbon atoms;
n is an integer from 1-2;
q is an integer from 1-3;
R' is a residue of a polyhydroxy compound having from 5-12 carbon atoms;
m is an integer from 2-6, useful as polyol reactants in the preparation of flame-retardant polyurethanes, are prepared by trans-acetalating a low molecular weight O,O-dialkyl phosphonoacetal with a polyhydroxy compound under acid catalysis.

10 Claims, No Drawings

PHOSPHORUS CONTAINING POLYOLS

FIELD OF THE INVENTION

The present invention is directed to new phosphorus containing polyols of high hydroxyl functionality, to their methods of preparation, and to their use as flame retardants, particularly in preparing fire retardant polyurethane compositions. The invention specifically relates to new polyhydroxylated lower O,O-dialkyl phosphenoacetals.

STATE OF THE PRIOR ART

Polyurethane foams have found wide and varied uses in industry. For example, the utility of flexible and semiflexible foams in cushioning and furniture construction and the great advantage of rigid foams in construction and insulation are now well-known. However, the range of utility of these foams has been somewhat limited by their flammability. Numerous attempts have, consequently, been made to impart flame retardance to these materials.

Polyurethane compositions containing various flame retardant additives are widely known. Most of these compositions contain non-reactive additives, that do not chemically combine with other constituents of the macromolecular chain. More recently there have appeared a number of reactive constituents, that chemically combine to form part of the polyurethane framework in the flame-retardant foam. In most cases, the reactive additive constitutes the polyol or polyester component of the system that ultimately forms the polyurethane macromolecular network. Thus phosphoric or phosphonic acid derivatives of polyols or polyester, optionally containing halogen, are known to impart flame retardancy to polyurethane compositions.

A major disadvantage of many such polyols is that they usually contain only two hydroxyl end-groups per polyester or polyol molecule. On the other hand, to produce the rigid foam structure a high functionality of hydroxyl groups is important. [See, for example, U.S. Pat. No. 3,726,855].

Some phosphorylated polymers containing high hydroxyl functionality are known. Tanabe and Ono [Japanese patent publication 56/10, 794 (C.A., 52:14,187e)] reported the fireproofing of polyvinyl alcohol fibers by treating the polymer with O,O-diethyl-2,2-dimethoxyethyl phosphonate. However, the subsequent phosphonic polyol polymer was not contemplated for use as a flame retardant additive. Levin and co-workers [Vysokomel Soedin., Ser. A, 12 (1970)574(C.A.73:4496w)] acetalated polyvinyl alcohol with O,O-diethyl phosphonacetaldehyde, producing a rubber like polymer, totally inadequate for the formation of a polyurethane foam. Heckles and Quinn [U.S. Pat. No. 3,764,570] prepared self-extinguishing and flame-retardant polyurethane foams by reacting conventional polyisocyanates with the reaction product of sugar polyols and phosphono-substituted carboxylic acid esters.

SUMMARY OF THE INVENTION

According to the invention there is provided a new class of phosphorus containing polyols of high hydroxyl functionality suited for use as reactive fire retardants particularly in polyurethanes. The new polyhydroxylated O,O-dialkyl phosphonoacetals of the present invention may be represented by the following formula:

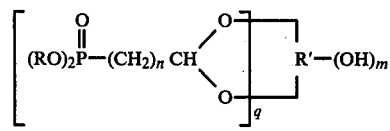

wherein
R is an alkyl group having from 1-3 carbon atoms;
n is an integer of 1 or 2,
q is an integer of 1 to 3,
R' is a residue of a polyhydroxy compound having from 5-20 carbon atoms and preferably 5-12 carbon atoms, not including the OH groups, and m is an integer of 0 to 6.

Examples of R falling within the scope of the present invention are methyl, ethyl, and propyl, with ethyl and methyl being preferred to maximize the phosphorus content of the ultimate polyol.

The new polyhydroxylated O,O-dialkyl phosphonoacetals of this invention may be prepared in a number of ways. They may be prepared by reacting a polyhydroxylated haloacetal, via the Arbusov reaction, with a trialkyl phosphite as follows:

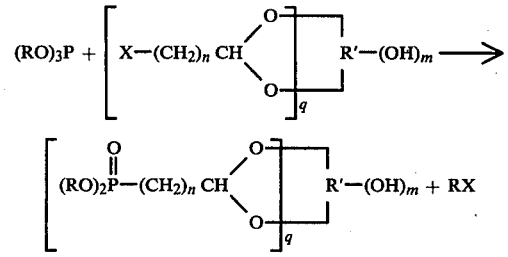

However, the preferred method for the preparation of the polyhydroxylated O,O-dialkyl phosphonoacetals according to the present invention is by means of transacetalating a low molecular weight O,O-dialkyl phosphonoacetal with a polyhydroxy compound under acid catalysis, with the elimination of the corresponding lower alkyl alcohol. The preferred process may be represented by the following equation:

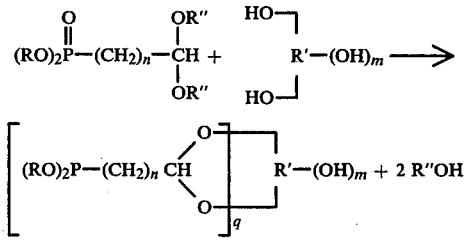

wherein R, n, q, and m are as previously defined and R" is a lower alkyl group having from 1-3 carbon atoms.

The polyhydroxy compounds which serve as starting materials for this invention can be any compound having sufficient hydroxy functionality so that at least two free hydroxy groups remain after reaction with the O,O-dialkyl phosphonoacetal, except that where the product is a bis-phosphonoacetal as in Example 4, there may be no free hydroxy groups left after the reaction.

Examples of polyhydroxy compounds falling within the scope of the present invention are monosaccharides and disaccharides and sugar alcohols, such as galactose, glucose, mannose, lactose, sucrose, dulcitol, mannitol and sorbitol; compounds such as erythritol, pentaerythritol, dipentaerythritol, tripentaerythritol, tetramethylolcyclohexanol, inositol; and the like.

The O,O-dialkyl phophonoacetals used as starting materials in the present invention may be prepared by the standard Arbuzov reaction between the corresponding trialkyl phosphites and the halogen substituted acetals, as described in the relevant literature.

The specific products obtained in the preferred method for preparing the new polyhydroxylated O,O-dialkyl phosphonoacetals of the present invention are dependent on the mole ratio of the reactants and the time of reaction.

In the preferred method, the reaction is conducted in a polar solvent such as water or dimethyl formamide. However, any inert solvent which dissolves the reactants but does not react with them may be used.

The preferred reaction is run in the presence of an acidic catalyst. When a polar organic solvent is used, the catalyst may be present in amounts of about 1% or more. In aqueous medium, however, higher concentrations of mineral acid catalyst are preferred. Suitable catalysts for use in the present invention include, for example, mineral acids, p-toluene sulfonic acids, acidic ion exchange resins, and the like.

The polyhydroxylated O,O-dialkyl phosphonoacetals of the present invention are recovered from the reaction mixture and purified by conventional methods. When the desired product separates as a solid it may be filtered, washed free of by-product and unreacted starting materials, and recrystallized from a suitable solvent.

DESCRIPTION OF THE PREFERRED EMBODIMENT

The following examples are illustrative of the process and products of the present invention, but are not to be construed in a limiting sense. All parts and percentages are by weight. In addition to the physical measurements listed below all products were also identified via their NMR and IR spectra.

EXAMPLE 1

To a mixture of 16 parts sorbitol and 49 parts O,O-diethyl-2,2-diethoxyethyl phosphonate in an open vessel was slowly added 15 parts concentrated hydrochloric acid while stirring the reaction mixture at room temperature. After twenty hours the mixture was neutralized with aqueous sodium hydroxide and about one-third of the water removed by evaporation. Extraction with 200 parts of toluene afforded 3.5 parts of unreacted O,O-diethyl-2,2-diethoxyethyl phosphonate, indicating a conversion of 93%. The reaction mixture was then extracted with 150 parts of chloroform, which yielded, upon evaporation of the chloroform, 37 parts (62%) of a yellow syrup of a mixture of O,O-diethyl phosphonoacetals of sorbitol with the following physical properties; n=1.4713; %P=10.5; Hydroxyl number=274. A further crop of mixed O,O-diethyl phosphonoacetals of sorbitol was obtained by evaporating the remaining mixture to dryness and extracting with methylene chloride which yielded, upon evaporation of the methylene chloride, 9 parts, $n_D$=1.4470; %P=9.1; Hydroxyl number 645.

Finely powdered KOH (0.8 parts) is added to the dry phosphono-acetal of sorbitol (11.75 parts, product of example 1), with stirring under nitrogen. The mixture is heated and at 140° C., propylene oxide (27.5 parts) is added dropwise during 30 minutes. Then 14.5 parts of trichlorobutylene oxide are added dropwise at 160° C. in 10 minutes. The reaction mixture was allowed to reflux at this temperature for 2.5 hours; After stripping off the unreacted components a viscous brown syrup (24 parts) was left. The oil was dissolved in a water (500 parts)—methanol (50 parts) mixture, stirred for 1 hour with Dowex 50W (50 parts) and afterwards 1 hour with Duolite A-6 (50 parts), concentrated, then decolorized by animal charcoal (1 part). The final product after vacuum evaporation is a viscous yellowish oil. $n_D^{20}$=1.484. % P 5.0; % Cl 22.4; OH number=410; $\eta$(30° C.)=1300 CP. This material was used in a standard formulation for polyurethanes, using diphenylmethane diisocyanate, resulting in a foam which showed considerable resistance to burning.

EXAMPLE 2

To a solution of 1 part mannose in 50 parts of dry N,N-dimethyl formamide in an open vessel are added 6.2 parts of O,O-diethyl-2,2-diethoxyethyl phosphonate and 0.1 parts of p-toluene sulfonic acid monohydrate while stirring and heating for three hours at 70° C. The mixture was then cooled and neutralized by stirring for one half hour with 10 parts of Amberlite IR-45 (OH). After filtration, the solvent was removed by heating to 70° C. and applying a vacuum. The remaining yellowish oil was dissolved in 25 parts of water and extracted with 100 parts chloroform. Evaporation of the chloroform afforded 3,8 parts of unreacted O,O-diethyl-2,2-diethoxyethyl phosphonate, indicating a conversion of 39%. The remaining aqueous solution was then evaporated to dryness to yield 1.2 parts (37%) of mono-O,O-diethyl phosphonoacetal of mannose, a yellow syrup with the following physical properties: $n_D$=1.4764; %P=7.4; Hydroxyl number=600.

EXAMPLE 3

Following the method of example 2, but using 25.4 parts O,O-diethyl-2,2-diethoxyethyl phosphonate and substituting 3.42 parts lactose in 150 parts of dry N,N-dimethyl formamide with a reaction time of 20 hours, there was obtained 8.4 parts (78% yield based on lactose and 28% conversion based on diethyl-2,2-diethoxyethyl phosphonate) of O,O-diethyl phosphonoacetal of lactose: $n_D$=1.4625; %P=7.8; Hydroxyl number=568.

EXAMPLE 4

The method of example 1, was followed by 6 parts of O,O-diethyl-2,2-diethoxyethyl phosphonate, 10 parts of concentrated hydrochloric acid, and 2.7 parts of pentaerythritol with a reaction time of 30 minutes were used. After neutralization the mixture was extracted with 300 parts toluene which yielded, upon evaporation, a white solid. Recrystallization from hexane/ethyl acetate (1:3) afforded 2.4 parts, m.p. 101°–102° C.; %P=12.4, which was shown by mass spectra to be the bis-O,O-diethyl phosphonoacetal of pentaerythritol. The remaining aqueous solution was found to contain crude mono-O,O-diethyl phosphonoacetal of pentaerythritol, %P=9.2, 3.7 parts. The overall yield of the phosphonated products came to 70%.

EXAMPLE 5

Following the method example 1, but using 6 parts of O,O-dimethyl-2,2-dimethoxyethylphosphonate, 20 parts of concentrated hydrochloric acid, and 2.5 parts of dulcitol the reaction was carried out for 24 hours at room temperature. After neutralization the mixture was evaporated to dryness and then extracted with several portions of hot alcohol. The alcohol was removed affording the crude product. Extraction of the crude material with hot benzene yielded upon evaporation 0.5 parts (8%) of the bis-O,O-dimethyl phosphonoacetal of dulcitol with a melting point (after recrystallization from ethanol/hexane) of 188°–190° C.; %P=13.7. The remaining benzene insoluble oil consisted of 4 parts of a mixture of mono-O,O-dimethyl phosphonoacetals of dulcitol with hydroxyl number=700.

We claim:

1. Polyhydroxylated O,O-dialkyl phosphonoacetals having the formula

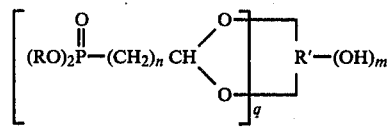

wherein
  R is an alkyl group having from 1–3 carbon atoms;
  n is an integer from 1–2;
  q is an integer from 1–3;
  R' is a residue of a polyhydroxy compound having from 5–12 carbon atoms;
  m is an integer from 0–6.

2. Compounds according to claim 1 wherein R is ethyl or methyl.

3. Compounds according to claim 1 wherein n is 1.

4. Compounds according to claim 1 wherein m is 2–6.

5. Compounds according to claim 4 wherein R' is a residue of sorbitol.

6. Compounds according to claim 4 wherein R' is a residue of mannose.

7. Compounds according to claim 4 wherein R' is a residue of lactose.

8. Compounds according to claim 4 wherein R' is a residue of pentaerythritol.

9. A compound according to claim 1 wherein m is 0.

10. A compound according to claim 9 which is bis-O,O-diethyl phosphonoacetal of pentaerythritol.

* * * * *